United States Patent
Unger et al.

Patent Number: 6,093,027
Date of Patent: *Jul. 25, 2000

[54] METHOD FOR THE SELECTION OF A FEMININE HYGIENE PRODUCT SYSTEM

[75] Inventors: Matthew Eric Unger, Hamilton; Thomas Ward Osborn, III; Alan Lawrence Maingot, both of Cincinnati; Holly Marie Zuziak, Norwood, all of Ohio; Carolyn Jeanne Miller, San Francisco, Calif.

[73] Assignee: The Procter & Gamble Company, Cincinnati, Ohio

[*] Notice: This patent is subject to a terminal disclaimer.

[21] Appl. No.: 08/854,612

[22] Filed: May 12, 1997

Related U.S. Application Data

[63] Continuation-in-part of application No. 08/656,941, May 30, 1996, abandoned.

[51] Int. Cl.[7] .............................. A47F 7/00; G09B 25/00; G09F 19/00
[52] U.S. Cl. ...................... 434/429; 434/430; 340/825.35
[58] Field of Search ...................................... 434/429, 377, 434/365, 273, 262, 238, 428, 430; 211/49.1; 340/825.35

[56] References Cited

U.S. PATENT DOCUMENTS

| | | |
|---|---|---|
| D. 371,707 | 7/1996 | Miles . |
| D. 372,272 | 7/1996 | Frisch . |
| 2,071,040 | 2/1937 | Lloyd . |
| 2,360,573 | 10/1944 | Mena . |
| 3,860,304 | 1/1975 | Bolton . |
| 4,064,880 | 12/1977 | Logan . |
| 4,181,176 | 1/1980 | Frazier . |
| 4,267,726 | 5/1981 | Noik . |
| 4,389,764 | 6/1983 | Flander et al. . |
| 4,429,806 | 2/1984 | Schwarzli . |
| 4,706,845 | 11/1987 | Schnurer et al. . |
| 4,750,640 | 6/1988 | Kobeck et al. . |
| 4,767,022 | 8/1988 | Oldorf . |
| 4,963,072 | 10/1990 | Miley et al. . |
| 5,047,947 | 9/1991 | Stump . |
| 5,167,345 | 12/1992 | Bleeker . |
| 5,178,169 | 1/1993 | Lamle . |
| 5,256,572 | 10/1993 | Tang et al. . |
| 5,467,285 | 11/1995 | Flinn et al. . |
| 5,520,203 | 5/1996 | Segerstrom ............................. 132/297 |
| 5,564,007 | 10/1996 | Kazen-Goudarzi et al. . |
| 5,564,547 | 10/1996 | Ranon et al. . |
| 5,639,235 | 6/1997 | Lapointe et al. . |
| 5,644,693 | 7/1997 | Fitzgerald et al. . |
| 5,691,919 | 11/1997 | Gemmell et al. . |
| 5,821,872 | 10/1998 | Brown et al. ...................... 340/825.35 |
| 5,839,585 | 11/1998 | Miller . |
| 5,862,947 | 1/1999 | Wiegner et al. .......................... 222/82 |
| 5,865,322 | 2/1999 | Miller . |
| 5,897,542 | 4/1999 | Lash et al. .............................. 604/378 |
| 5,947,502 | 9/1999 | Miller ..................................... 434/430 |

FOREIGN PATENT DOCUMENTS

| | | |
|---|---|---|
| 1356956 | 2/1964 | France . |
| 805 066 | 7/1951 | Germany . |
| 31 44944 A1 | 5/1983 | Germany . |
| 3641614 A1 | 6/1988 | Germany . |
| 1 303 79 | 2/1929 | Switzerland . |
| 2 271 559 | 4/1994 | United Kingdom . |

*Primary Examiner*—Jessica J. Harrison
*Attorney, Agent, or Firm*—Matthew P. Fitzpatrick; Jeffrey V. Bamber

[57] ABSTRACT

A method for the selection and use of a system of feminine hygiene products is described. The method includes an information collection step, a system selection step, and an information provision step. In the information collection step, information is collected from a consumer regarding her body type and menstrual cycle characteristics. In the system selection step, the information collected is used to select a system of feminine hygiene products from at least two of such available systems. Each of such available systems is comprised of at least two different feminine hygiene products. Additionally, each of said available systems is adapted to correspond to a predetermined range of body types and menstrual cycle characteristics. In the information provision step, information identifying the system of products selected is then provided to the consumer allowing her to use the system of feminine hygiene products.

31 Claims, 2 Drawing Sheets

6,093,027

METHOD FOR THE SELECTION OF A FEMININE HYGIENE PRODUCT SYSTEM

This is a continuation in part of application Ser. No. 08/656,941, filed May 30, 1996, abandoned.

FIELD OF THE INVENTION

The present invention is directed to a method for the selection and use of a system of feminine hygiene products. More particularly, the present invention is directed to a method in which information is collected from a consumer regarding certain of her physical characteristics and regarding certain aspects of her menstrual cycle. The information collected is used to select a particular system of feminine hygiene products from a group of two or more available systems. The system of products selected is then revealed to the consumer for use by the consumer to achieve a reduction in soiling as compared to the use of a single type of feminine hygiene product.

BACKGROUND OF THE INVENTION

Feminine hygiene products such as sanitary napkins, pantiliners, and incontinence pads are devices that are typically worn in the crotch region of an undergarment. Interlabial devices are feminine hygiene products that are typically designed to be worn within the interlabial space of a wearer. Other feminine hygiene devices such as tampons are designed to be worn within the vaginal interior. All of these devices are designed to absorb or otherwise contain liquid and other discharges from the human body and to prevent body and clothing soiling. Sanitary napkins are a type of absorbent article worn by women in a pair of panties that is normally positioned between the wearer's legs, adjacent to the perineal area of the body.

Feminine hygiene products having many different basic designs are known in the art. There are some key features of these products, however, which affect the performance of such products. For example, feminine hygiene products such as sanitary napkins vary in their absorbent capacities, their length, the area of undergarment which they cover, their thicknesses, and their inclusion or non-inclusion of certain features such as wings or flaps.

Currently, feminine hygiene products such as sanitary napkins are typically sold in packages containing quantities of ten to fifty products of a single product type. As a result, many consumers buy and use a single type of product for all their menstrual protection needs. This is the case even though the characteristics (e.g. length, area, and features) of a feminine hygiene product necessary to provide containment of bodily fluids without leaking may be quite different between daytime and overnight use. Similarly, the characteristics of a feminine hygiene product necessary to contain bodily fluids without leaking will vary for different groups of consumers based on such factors as body size and menstrual cycle characteristics.

Further complicating the present situation with respect to feminine hygiene products is the fact that the number of different types of products available often makes it confusing for consumers to determine which products would best meet their protection needs. In a recent survey of a typical retail store, 103 different types of feminine hygiene products were on display for sale to consumers. In another recent survey, roughly 70% of consumers reported purchasing the wrong type of sanitary napkin and/or pantiliner at least once within the six month period preceding the survey.

It has been found in developing the present invention, that use by the consumer of a system of feminine hygiene products provides her with superior protection and comfort as compared to the use of a single type of product for all menstrual protection purposes. Nevertheless, the sheer number of options available makes the selection of an appropriate system difficult. Based upon the numbers of different types of products currently available for sale, it is estimated that there are well over 10,000 possible combinations of systems which contain only two different types of feminine hygiene products. When systems including more than two different products are considered, the number increases geometrically.

Ideally, an appropriate system of feminine hygiene products is chosen from two or more available systems where each of such systems is designed for a particular group of consumers. Membership in a particular group is based upon factors such as body size and menstrual cycle characteristics.

It has also been found during the development of the method of the present invention that many women (especially those who do not truly have a heavy flow intensity) are not proficient in accurately describing their flow intensity as compared to other consumers. Most currently available feminine hygiene products describe the differences between the various available products only in terms of a consumer's assessment of her own flow intensity or overall protection needs. It has been found that better product selection of systems of feminine hygiene products can be obtained by the method of the present invention which relies at least in part on indicators of protection needs other than simply perceived flow. Ideally, at least some of these indicators are objective pieces of information which should be readily known to most consumers. In this manner, consumers can be more reliably be provided with appropriate systems of feminine hygiene products without having to guess as to which products will best suit their needs. An ideal method for the selection and use of a system of feminine hygiene products also eliminates the need for consumers to select systems solely on the basis of subjective (and often inaccurate indicators) such as self-perception of flow intensity alone.

Therefore, it is an object of the present invention to provide a method for the selection and use of a system of feminine hygiene products.

It is another object of the present invention to provide a method for the selection of a system of feminine hygiene products from two or more available systems, the selection being based upon information gathered from the consumer regarding at least her body size and preferably certain characteristics related to her menstrual cycle.

It is also an object of the present invention to provide a method for the selection and use of system of feminine hygiene products which system is adapted for a particular group of consumers and which when used will achieve a reduction in the incidence of soiling as compared to the use of a single type of feminine hygiene product.

It is a further object of the present invention to provide a reliable method for the selection and use of an appropriate system of feminine hygiene products in which the information gathered from consumers includes at least some objective pieces of information which are expected to be known by a majority of consumers.

These and other objects of the present invention will become more readily apparent when considered in reference to the following description and when taken in conjunction with the accompanying drawings.

SUMMARY OF THE INVENTION

The present invention is directed to a method for the selection and use of a system of feminine hygiene products. More particularly, the present invention is directed to a method in which information is collected from a consumer regarding her body size and menstrual cycle characteristics. The information collected is used to select a system of feminine hygiene products from at least two of such available systems. Each of such available systems is comprised of at least two different feminine hygiene products. Additionally, each of said available systems is adapted to correspond to a predetermined range of body sizes and menstrual cycle characteristics. Information identifying the system of products selected is then provided to the consumer allowing her to use the system of feminine hygiene products.

In a preferred embodiment, there are four available systems of feminine hygiene products comprising sanitary napkins. The first of these systems is adapted for use by women with light protection needs. The second of four available systems in this preferred embodiment is adapted for use by women with light to moderate protection needs. The third of the four systems in this preferred embodiment is adapted for use by women with moderate to heavy protection needs. The fourth of the four available systems in this preferred embodiment is adapted for use by women with heavy to very heavy protection needs. Protection needs are a function of body size and menstrual cycle characteristics.

In preferred embodiments, the collection of information from a consumer and the selection of a system of feminine hygiene products may be performed using a computer, an interactive display, a telephone system, published questionnaires, or through literature distributed to health care providers.

In another preferred embodiment, the provision of information to the consumer regarding the products which make up the system of feminine hygiene products may be accomplished through the use of packaging indicia. Each system of feminine hygiene products containing at least two different kinds of feminine hygiene products may be packaged in a common package which is made available to the consumer.

In preferred embodiments of the present invention, the use of a system of feminine hygiene products provides a reduction in the incidence of soiling as compared to the use of a single type of feminine hygiene product.

BRIEF DESCRIPTION OF THE DRAWING

While the specification concludes with claims particularly pointing out and distinctly claiming the subject matter which is regarded as forming the present invention, it is believed that the invention will be better understood from the following description taken in conjunction with the accompanying drawing, in which:

DETAILED DESCRIPTION OF THE INVENTION

The present invention is directed to a method for the selection and use of a system of feminine hygiene products. The method of the present invention comprises three steps: collecting information from a consumer regarding her body size and menstrual cycle characteristics, selecting an appropriate system of feminine hygiene products from a group of two or more available systems of products, and providing information to the consumer identifying the products which make up the selected system allowing her to use the system of feminine hygiene products.

Figure 1:
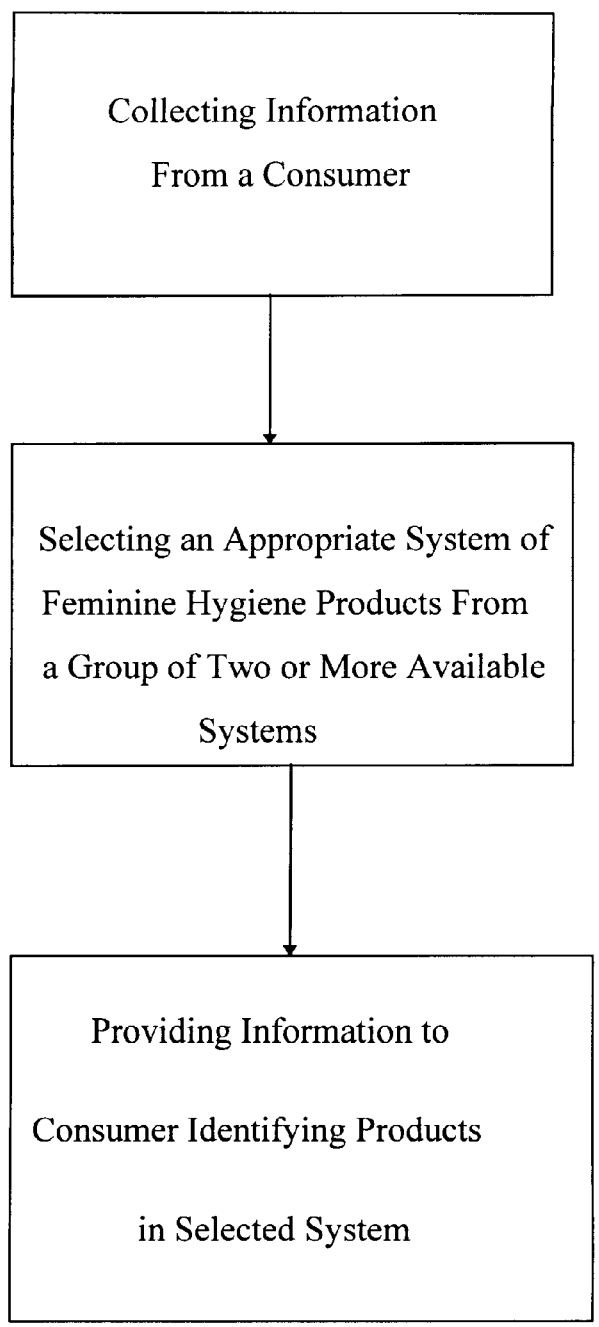
FIG. 1 is flow diagram representing the steps of a method according to the present invention.

FIG. 1 is a flow diagram representing the steps of a method according to the present invention.

As used herein the term "feminine hygiene products" refers to disposable absorbent articles used by women for catamenial protection. Such products include sanitary napkins, tampons, interlabial products, incontinence devices, and pantiliners. The term "disposable" is used herein to describe absorbent articles which are not intended to be laundered or otherwise restored or reused as an absorbent article (i.e., they are intended to be discarded after a single use, and, preferably, to be disposed of in an environmentally compatible manner). As used herein, the term "absorbent article" refers to devices which absorb and contain body exudates, and, more specifically, refers to devices which are placed within, against, or in proximity to, the body of the wearer to absorb and contain the various exudates discharged from the body.

The term "system" as used herein refers to a group of at least two feminine hygiene products. Each of the products within such a group is chosen to best serve the protection needs of consumers falling within a predetermined range of body sizes and menstrual flow characteristics. For example, one system of feminine hygiene products might be adapted for use by small women with moderate protection needs. A system for consumers in such a category might include sanitary napkins for use during regular need times within a menstrual cycle and sanitary napkins of a different type for use during increased need times within a menstrual cycle (for example, overnight).

It has been found during development of the present invention that certain key pieces of information regarding the body size and menstrual flow characteristics of a particular woman may be used to assist her in the selection of a system of feminine protection products which is particularly adapted to her needs. The use of such an adapted system will preferably achieve a reduction in the incidence of soiling as compared to the use of a single type of feminine hygiene product.

In a preferred embodiment of the present invention, there are four predetermined ranges of body sizes and menstrual flow characteristics as well as four or more available systems of feminine hygiene products. Each range of body sizes and menstrual flow characteristics has at least one corresponding system of feminine hygiene products which is specifically adapted for use by consumers within that range. An individual consumer is placed in the appropriate range based upon information collected from the consumer.

Table 1 is a table which shows four possible topics of information which may be collected from consumers to carry out the method of the present invention.

TABLE 1

|  |  | category 1 | category 2 | category 3 | category 4 |
|---|---|---|---|---|---|
| FLOW INTENSITY | 1 | light | light to moderate | moderate to heavy | heavy to very heavy |
|  | 2 | light | moderate | heavy | very heavy |
|  | 3 | birth control: pill | birth control: none | birth control: IUD | birth control: IUD |
|  | 4 | age: <25 years | age: 25 to 30 years | age: 31 to 40 years | age: >40 years |
|  | 5 | pregnancies: 0 | pregnancies: 1–3 | pregnancies: 3 to 4 | pregnancies: 5 or more |
| PERIOD DURATION AND VOLUME | 1 | light | moderate | heavy | very heavy |
|  | 2 | less than 3 days | 3 to 4 days | 4 to 5 days | more than 5 days |
|  | 3 | <40 g menses/period | 30 to 60 g menses/period | 50 to 80 g menses/period | >70 g menses/period |
|  | 4 | 0 heavy days/nights | <2 heavy days/nights | 2 to 4 heavy days/nights | >4 heavy days/nights |
| BODY SIZE | 1 | petite body | small body | medium body | large body |
|  | 2 | petite panty size | small panty size | medium panty size | large panty size |
|  | 3 | panty size less than 5 | panty size 5 to 7 | panty size 8 to 10 | panty size 11 to 15 |
|  | 4 | hips <32 inches | hips 32 to 41 inches | hips 41 to 47 inches | hips 47 inches or more |
|  | 5 | petite to small clothing size | small to medium clothing size | medium to large clothing size | large to plus clothing size |
| SOILING PATTERN | 1 | rarely soil ends/sides | occassionally soil ends/sides | often soil ends/sides | almost always soil ends/sides |
|  | 2 | soils <8% of changes | soils 8 to 10% of changes | soils 10 to 15% of changes | soils >15% of changes |
|  | 3 | 0 soils per period | 1 to 2 soils per period | 2 to 4 soils per period | 4 or more soils/period |

As shown in Table 1, the topics of information collected from a consumer preferably refer to her body size, her flow intensity, her period duration and volume, and experienced soiling pattern. The topics shown in Table 1 are separated into 4 different levels or categories. The consumer is prompted in any suitable manner (e.g., through the answering of questions printed on a chart or interactive display screen) to provide sufficient information to place her in one of the four levels or categories for each of topics shown in Table 1 (i.e. body size, flow intensity, period duration and volume, and soiling pattern). For example, in order to determine the proper category for a particular consumer with respect to body size, a consumer may be asked to chose her body size from the following list: petite body, small body, medium body, large body, where the responses correspond to body size categories 1, 2, 3, and 4, respectively.

Various other questions may be used either individually or in combination to place a particular consumer in one of the four body size categories. Consumers in body size category 1, will generally describe their body size and/or panty size as petite. In the United States this corresponds to a panty size of less than about 5. The hip size of consumers in this category will generally be smaller than about 32 inches (81 cm). Consumers in body size category 2 will generally describe their body and/or panty size as small. This corresponds in the United States to a panty size of about 5 to 7. The hip size of consumers in this category will generally range from about 32 to 41 inches (81 to 104 cm). Consumers in body size category 3 will generally describe their body and/or panty size as medium. This corresponds to a panty size of about 8 to 10 in the United States. The hip size of consumers in this body size category will range from about 41 to 47 inches (104 to 119 cm). Consumers in body size category 4 generally describe their body and/or panty size as large. This corresponds to a panty size in the United States of about 11 to 15. The hip size of consumers in this category is about 48 inches (122 cm) or more.

Another indicator of body size is clothing size in general (as opposed to simply panty size). Certain consumers may be more familiar with their clothing size in general or their size for particular types of clothing than they may be with their panty size. Additionally, certain consumers may be more comfortable with being prompted for clothing size information rather than panty size information. Therefore, in some embodiments of the method of the present invention it may be preferable to collect information from consumers regarding clothing size either instead of or in addition to panty size. Clothing size information could include dress size, slack or pants size, or the size of any clothing that will generally cover the lower half of a person's body. For example, as shown in Table 1, consumers in body size category 1 might describe their clothing size as "petite to small." Consumers in body size category 2 might describe their clothing size as "small to medium." Consumers in body size category 3 might describe their clothing size as "medium to large." Consumers in body size category 4 might describe their clothing size as "large to plus size."

Other commonly used indicators of body size such as the Body Mass Index could also be adapted to the method of the present invention for use in collecting body size information from a consumer. A discussion of Body Mass Index is included in the August, 1996 issue of *Scientific American.*

One skilled in the art will readily appreciate that numerous combinations of either individual questions or groups of questions may be asked in order to collect sufficient information to place a consumer in one of these categories with respect to body size. The precise manner and wording chosen to collect this information from the consumer may vary depending on local custom, the comfort level consumers in a particular area may have in describing their body size or menstrual flow characteristics, and the shades of meaning associated with terms which may be used in different parts of the world to collect the information desired.

In addition to collecting information regarding the body size of a consumer, the preferred embodiment shown in Table 1 also shows information which may be used to place a consumer in one of four categories with respect to flow intensity. Indicators of the proper flow intensity category for a given consumer include age, type of birth control used, number of pregnancies, and the consumer's self-perception of her flow intensity.

Consumers in flow intensity category 1 will generally have a light perceived flow. Additionally, they may be under about 25 years of age, may use birth control pills, and/or may have never been pregnant.

Consumers in flow intensity category 2 will generally have a "light to moderate" (or simply "moderate") perceived flow. These consumers may range in age from about 25 to about 30 years, may not use birth control, and/or may have been pregnant 1–3 times.

Consumers in flow intensity category 3 will typically have a "moderate to heavy" (or simply "heavy") perceived flow. These consumers may range in age from about 31 to about 40 years, may use an IUD as birth control, and/or may have been pregnant 3–4 times.

Consumers in flow intensity category 4 will typically have a "heavy to very heavy (or simply "very heavy") perceived flow. This category of consumers may be older than about 40 years of age, may use an IUD as birth control, and/or may have been pregnant 5 or more times.

These broad classifications of age, type of birth control used, and number of pregnancies are not intended to be absolute indicators of the proper flow intensity category. Rather, this information represents a variety of conditions which impact flow intensity for many consumers. Such information is useful to assist many consumers in placing themselves in the proper flow intensity category if they are uncertain how to benchmark their perceived flow intensity.

Table 1 also shows information which may be used to place a consumer in one of four categories with respect to period duration and volume. Indicators of the proper period duration and volume category for a given consumer include the total number of days within a cycle that the consumer typically menstruates, the number of "heavy" days or nights a consumer experiences within a typical cycle, and the consumer's self perception of her period duration and volume.

Consumers in period duration and volume category 1 will generally menstruate for less than 3 days in a cycle, and may not experience any heavy days or nights. These consumers will typically perceive their period duration and volume as "light." The overall amount of menses discharged by consumers in this category is less than about 40 grams per period.

Consumers in period duration and volume category 2 will generally menstruate for approximately 3 to 4 days in a cycle, and may experience less than about 2 heavy days or nights. These consumers will typically perceive their period duration and volume as "moderate." The overall amount of menses discharged by consumers in this category is between about 30 and about 60 grams per period.

Consumers in period duration and volume category 3 will generally menstruate for about 4 to 5 days, and may experience about 2 to 4 heavy days or nights. These consumers will typically perceive their period duration and volume as "heavy." The overall amount of menses discharged by consumers in this category is about 50 to about 80 grams per period.

Consumers in period duration and volume category 4 will generally menstruate for more than about 5 days, and may experience 4 or more heavy days or nights. These consumers will typically perceive their period duration and volume as "very heavy." The overall amount of menses discharged by consumers in this category is greater than about 70 grams per period.

Another indicator of period duration and volume category is the number of times in a typical cycle a consumer replaces a used feminine hygiene product with a fresh one. Related to this indicator is the loading of a product before it is replaced with a fresh product. The typical loading for a feminine hygiene product before replacement tends to vary by regional practices and customs. Therefore, the use of number of fresh products used in a cycle as an indicator of period duration and volume should take typical regional practices and customs into account.

Figure 2:
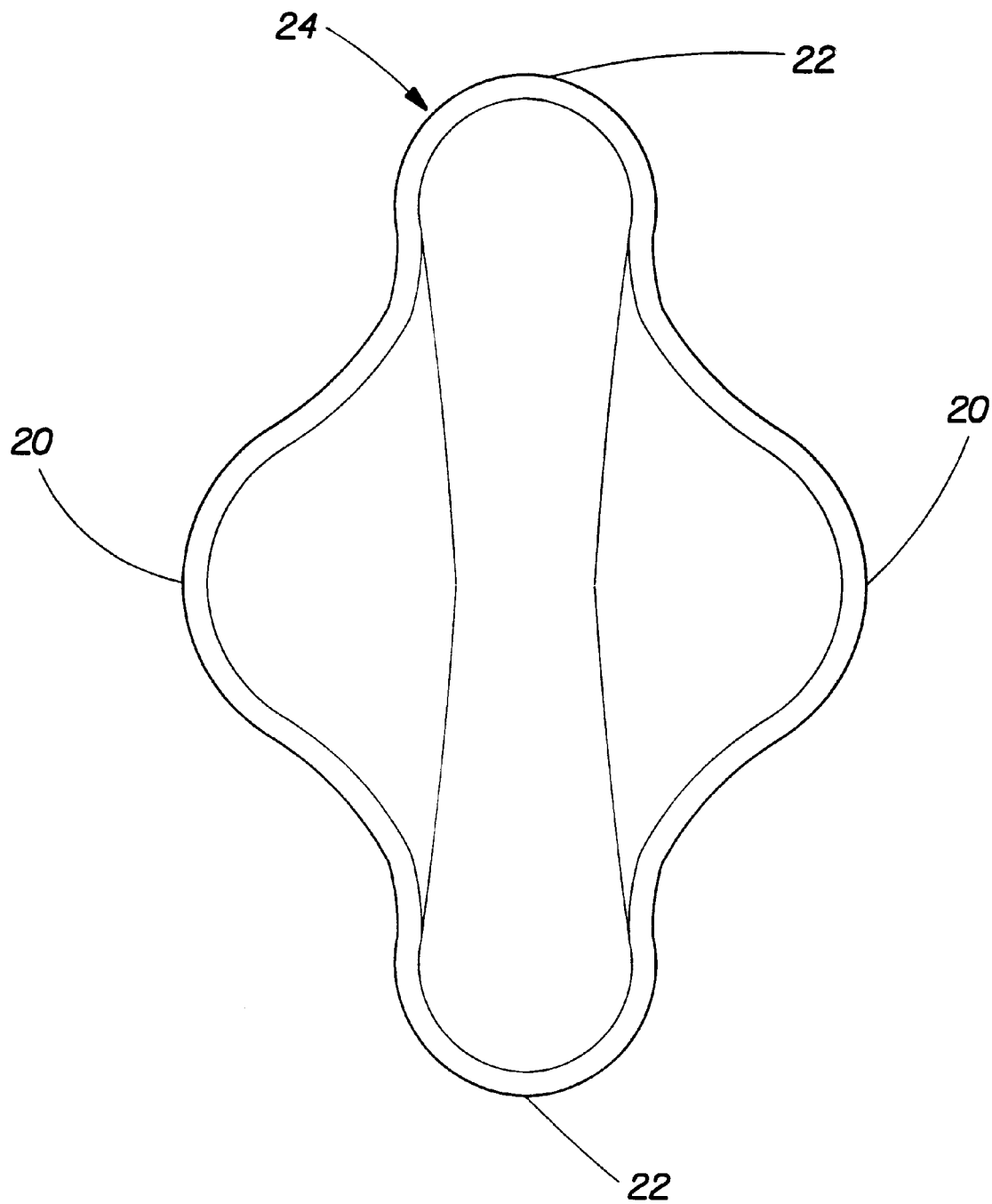
FIG. 2 is a typical prior art sanitary napkin showing the location of the side edges and end edges of the sanitary napkin.

Also shown in Table 1 is information which may be used to place a consumer in one of four categories with respect to experienced soiling pattern. Using currently available sanitary napkins, many consumers may experience side soiling or end soiling with varying frequency. FIG. 2 shows a typical prior art sanitary napkin 24 and the locations on the top of the sanitary napkin 24 where side soling or end soiling might occur. The term "side soiling" refers to the soiling of the side edges 20 of a sanitary napkin 24 when the sanitary napkin is used by a consumer. The term "end soiling" refers to the soiling of the end edges 22 of a sanitary napkin 24 when the sanitary napkin is used by a consumer.

Consumers in soiling pattern 1 will "rarely" experience side or end soiling when using currently marketed sanitary napkins (that is, these consumers will experience soils in less than about 8% of pad changes). These consumers will typically experience no undergarment soils per period. Consumers in soiling pattern category 2 will "occasionally" experience side or end soiling when using currently marketed sanitary napkins (that is, these consumers will experience soils in about 8 to about 10% of pad changes). These consumers may experience about 1 to 2 soils per period. Consumers in soiling pattern category 3 will "often" experience side or end soiling when using currently marketed sanitary napkins (that is, these consumers will experience soils in about 10 to about 15% of pad changes). These consumers may experience about 2 to 4 soils per period. Consumers in soiling pattern category 4 will "almost always" experience side and/or end soiling when using currently marketed sanitary napkins (that is, these consumers will experience soils in greater than about 15% of pad changes). These consumers may experience about 4 or more soils per period.

As in the case with body size, one skilled in the art will appreciate that numerous combinations of either individual questions or groups of questions may be asked to place a consumer in one of these categories with respect to flow intensity, period duration and volume, and soiling pattern.

In the preferred embodiment of the present invention shown in Table 1, information is collected with respect to the four topics shown (i.e. body size, flow intensity, period duration and volume, and soiling pattern). It has been found during the development of the present invention that the most important of these is body size. Therefore, in more preferred embodiments of method of the present invention, information regarding the body size of the consumer should always be collected from the consumer.

It has also been found during the development of the present invention that the information pertaining to flow intensity and to period length and volume are closely related. As a result, a majority of consumers are expected to fall into the same category for both the flow intensity and the period length and volume categories. Although this is the case, as noted previously, a consumer's self-perception of her flow is often not an accurate indicator of her "true" flow intensity (i.e., the property category as compared to other consumers). Therefore, in more preferred embodiments of the method of the present invention, the proper flow intensity category for a particular consumer may be ascertained by asking that consumer to describe her perceived flow intensity from a list consisting of: "light", "moderate", "heavy", and "very heavy". An alternative list could consist of: "light", "light to moderate", "moderate to heavy", and "heavy to very heavy." In these more preferred embodiments, if information regarding perceived flow intensity is elicited from the consumer in the manner described above, then the questions or prompts used to collect information from the consumer regarding period length and volume should be more objective (as opposed to relating to the consumer's self-perception). For example, if flow intensity information is collected by asking a consumer to chose which term from either of the lists given above best describes her flow intensity, then period length and volume information could be collected by asking a consumer how long she menstruates in a typical cycle and/or how many heavy days or nights she experiences in a typical cycle.

Using questions which relate to facts which are objective and which are expected to be known by a given consumer helps to ensure that the consumer will be placed into the proper category for each of the topics shown in Table 1. This particular predetermined range of body types and menstrual cycle characteristics. Table 2 is a table showing how in a preferred embodiment of the method of the present invention, the information collected from using Table 1 may be used to select one of four systems which are available in this preferred embodiment.

TABLE 2

|  | column 1 all answers 1 point | column 2 all answers 2 points | column 3 all answers 3 points | column 4 all answers 4 points |
| --- | --- | --- | --- | --- |
| FLOW INTENSITY | flow category 1 | flow category 2 | flow category 3 | flow category 4 |
| PERIOD DURATION AND VOLUME | period category 1 | period category 2 | period category 3 | period category 4 |
| BODY SIZE | body size category 1 | body size category 2 | body size category 3 | body size category 4 |
| SOILING PATTERN | soiling category 1 | soiling category 2 | soiling category 3 | soiling category 4 |
| Please add your answers from each colored column |  |  |  |  |
| points | System 1 4 to 6 | System 2 7 to 10 | System 3 11 to 13 | System 4 14 to 16 | approach also reduces reliance on subjective assessments by consumers (such as self-perception of flow without further verification) which are often inaccurate.

It has been found that a majority of consumers will tend to fall into the same category (i.e., 1, 2, 3, or 4) or close to the same category for each of the four topics shown. Nevertheless, in the preferred embodiment shown in Table 1, information relating to all four topics is collected from the consumer in order to appropriately place those smaller numbers of consumers who fall into significantly different categories for some of the topics shown. Additionally, the use of all of the topics shown in Table 1 helps to ensure that small differences in category placement among similar consumers which may result from misperceptions or varying meanings assigned to terms used to collect the information will be diminished in importance. Consequently, consumers with similar protection needs will ultimately have similar systems of feminine hygiene products selected for them.

In variations of the preferred embodiment shown in Table 1, information regarding fewer than all four topics shown may be collected while still carrying out the method of the present invention. For example, the information may be collected from the consumer regarding only her body size. Similarly, information regarding body size and flow intensity only may be collected. Other acceptable combinations include, but are not limited to, body size and period duration and volume information; body size and soiling information; and body size, flow intensity, and period duration and volume information. Because flow intensity and period duration and volume are closely related, these categories may be combined in a variation of the preferred embodiment shown in Table 1.

Once information is collected from a consumer regarding her body type and menstrual cycle characteristics, a system of feminine hygiene products is selected from at least two of such available systems. Each of such available systems contains at least two feminine hygiene products of different types. Similarly, each system is adapted to correspond to a After having collected the information shown in Table 1, a given consumer will have been placed in one of four categories for each of the following topics: body size, flow intensity, period duration and volume, and soiling pattern. While many method of "scoring" might be envisioned, a preferred method is shown in Table 2. As shown in Table 2, category 1 for each topic is assigned a point value of 1, category 2 for each topic is assigned a point value of 2, category 3 for each topic is assigned a point value of 3, and category 4 for each topic is assigned a point value of 4. The points from each topic are added to yield a total score ranging from 4 to 16. This point total is used to select one of four systems which are available in this preferred embodiment of the method of the present invention.

In the preferred embodiment shown in Table 2, point totals from 4 to 6 correspond to System 1, point totals from 7 to 10 correspond to System 2, point totals from 11 to 13 correspond to System 3, and point totals from 14–16 correspond to System 4. The points may be added by the consumer with or without the assistance of a chart similar to that in Table 2. Alternatively, the points may be added by a computer or other calculation device, or though the assistance of a modified slide-rule type device (for example, a dial or wheel on a store display).

Alternative preferred embodiments for selecting one of four available systems of feminine hygiene products are shown in Table 3 and Table 4.

TABLE 3

| PERIOD or FLOW | body size, category 1 | body size, category 2 | body size, category 3 | body size, category 4 |
|---|---|---|---|---|
| category 1 | System 1 | System 1 | System 2 | System 3 |
| category 2 | System 1 | System 2 | System 2 | System 3 |
| category 3 | System 2 | System 2 | System 3 | System 4 |
| category 4 | System 2 | System 3 | System 4 | System 4 |

In the preferred embodiment shown in Table 3, information is collected from a consumer regarding her body size and either her period duration and volume or flow intensity information as described above. This information is used to place the consumer in one of four categories with respect to body size and period duration and volume or flow intensity as described above and shown in Table 1. The chart in Table 3 shows how the combination of the body size category and either the period or flow category for a particular consumer may be used to arrive at a selection of one of four available systems of feminine hygiene products.

TABLE 4

| PERIOD or FLOW | body size, category 1 | body size, category 2 | body size, category 3 | body size, category 4 |
|---|---|---|---|---|
| category 1 | system 1 | | | |
| category 2 | | system 2 | | |
| category 3 | | | system 3 | |
| category 4 | | | | system 4 |

Table 4 is similar to Table 3, but shows a table which shows less defined boundaries between each of the four available systems of feminine hygiene products. In alternative embodiments of the method of the present invention a table similar to that shown in Table 4 might appear on a store display. Use of such a table may require a consumer to chose between one of two possible systems if she is located in a combination of body size and flow or period categories which places her near the boundary of two feminine hygiene product systems.

In a preferred embodiment of the method of the present invention, there are four available systems of feminine hygiene products. Each of the four systems in this preferred embodiment is comprised of at least two different types of sanitary napkins. Each system preferably contains at least one sanitary napkin product for use during regular need times in a given menstrual cycle. Additionally, each system preferably contains at least one sanitary napkin product for use during heavy need times (such as overnight, or on heavy flow days) in a given menstrual cycle. As described above, each of the four available systems in this preferred embodiment is adapted for use by consumers within a particular range of body size and menstrual cycle characteristics.

System 1 is adapted for use by women with light protection needs. In a preferred embodiment of the present invention, System 1 includes a sanitary napkin product with a length of between about 110 and about 244 mm, more preferably between about 219 and about 230 mm, and an area of between about 55 and about 242 cm$^2$, more preferably between about 162 and about 242 cm$^2$, for regular need times. Likewise, in this preferred embodiment, System 1 also includes a sanitary napkin product with a length of between about 219 and about 249 mm, and an area of between about 126 and about 265 cm$^2$, more preferably between about 162 and about 265 cm$^2$, for heavy need times. Methods for measuring the area and length of a sanitary napkin are described in the test methods section, below.

System 2 in this preferred embodiment is adapted for use by women with light to moderate protection needs. Preferably, System 2 includes a sanitary napkin with a length of between about 219 and about 249 mm, and an area of between about 126 and about 224 cm$^2$, more preferably between about 162 and about 224 cm$^2$, for regular need times. In this preferred embodiment, System 2 also includes a sanitary napkin product with a length of between about 226 and about 261 mm, more preferably between about 238 and about 261 mm, and an area between about 146 and about 320 cm$^2$, more preferably between about 220 and about 320 cm$^2$, for heavy need times.

System 2 may contain at least one sanitary napkin product with panty elastic wrapping components. The term "panty elastic wrapping components" includes, but is not necessarily limited to: "wings," such as those described in U.S. Pat. Nos. B1 4,589,876 and 4,687,478; side wrapping elements which automatically wrap the side edges of the wearer's panties when the panties are pulled up by the wearer, such as those described in U.S. Pat. No. 5,558,663; flaps with zones of extensibility such as those described in U.S. Pat. No. 5,354,400; or tabs.

System 3 in this preferred embodiment is adapted for use by women with moderate to heavy protection needs. Preferably, System 3 includes a sanitary napkin with a length of between about 232 and about 261 mm, more preferably between about 238 and about 261 mm, and an area of between about 146 and about 320 cm$^2$, more preferably between about 255 and about 320 cm$^2$, for regular need times. In this preferred embodiment, System 3 also includes a sanitary napkin product with a length of between about 248 and about 304 mm, more preferably between about 255 and about 304 mm, and an area between about 177 and about 348 cm$^2$, more preferably between about 302 and about 348 cm$^2$. Preferably, System 3 contains at least one sanitary napkin product which includes panty elastic wrapping components.

System 4 in this preferred embodiment is adapted for use by women with heavy to very heavy protection needs. Preferably, System 4 includes a sanitary napkin with a length of between about 248 and about 304 mm, more preferably between about 255 and about 304 mm, and an area between about 170 and about 348 cm$^2$, more preferably between about 302 and about 348 cm$^2$, for regular need times. In this preferred embodiment, System 4 also includes a sanitary napkin product with a length of about 296 mm or more, more preferably between about 300 and about 380 mm, and an area of about 224 cm$^2$ or more, more preferably between about 314 and about 500 cm². Preferably, System 4 contains at least one sanitary napkin product which includes panty elastic wrapping components.

The Procter & Gamble Company of Cincinnati, Ohio, manufactures commercially available sanitary napkin products which are suitable for inclusion in each of the systems of the preferred embodiment described above for both regular protection needs and heavy protection needs. The following products are suitable for inclusion in System 1 for regular protection needs: ALWAYS® Ultra thin Slender Maxi with Wings sanitary napkin which is manufactured and packaged under one or more of U.S. Pat. No. 4,342,314, 4,463,045, 4,556,146, B1 4,589,876, 4,687,478, 4,950,264, 5,009,653, 5,267,992, and U.S. Pat. No. Re. 32, 649; and ALWAYS® Thin Maxi sanitary napkin which is manufactured and packaged under one or more of U.S. Pat. Nos. 4,342,314, 4,463,045, 4,556,146, 4,573,986, 5,413,568, and 5,462,166. Likewise, the following products are suitable for inclusion in System 1 for heavy protection needs: ALWAYS® Thin Maxi with Wings sanitary napkin which is manufactured and packaged under one or more of U.S. Pat. No. 4,342,314, 4,463,045, 4,556,146, 4,573,986, B1 4,589, 876, 4,687,478, 5,267,992, 5,413,568, 5,462,166, and 5,489, 283; ALWAYS® Ultra thin Maxi sanitary napkin which is manufactured and packaged under one or more of U.S. Pat. Nos. 4,342,314, 4,463,045, 4,556,146, 4,950,264, 5,009, 653, 5,413,568, 5,460,623, 5,462,166, 5,569,231, and U.S. Pat. No. Re. 32,649; and ALWAYS® Regular Maxi sanitary napkin which is manufactured and packaged under one or more of U.S. Pat. Nos. 4,342,314, 4,463,045, 4,556,146, 4,573,986, 5,413,568, and 5,462,166.

Suitable products for inclusion in System 2 for regular protection needs include ALWAYS® Ultra thin Maxi sanitary napkin and ALWAYS® Regular Maxi sanitary napkin. The following products are suitable for inclusion in System 2 for heavy protection needs: ALWAYS® Ultra thin Maxi with Wings sanitary napkin which is manufactured and packaged under one or more of U.S. Pat. Nos. 4,342,314, 4,463,045, 4,556,146, B1 4,589,876, 4,687,478, 4,950,264, 5,009,653, 5,267,992, 5,413,568, 5,460,623, 5,462,166, 5,489,283, 5,569,231, and U.S. Pat. No. Re. 32,649; and ALWAYS® Regular Maxi with Wings which is manufactured and packaged under one of more of U.S. Pat. Nos. 4,342,314, 4,463,045, 4,556,146, 4,573,986, B1 4,589,876, 4,687,478, 5,267,992, 5,413,568, 5,462,166, and 5,489,283.

Suitable products for inclusion in System 3 for regular protection needs include ALWAYS® Ultra thin Maxi with Wings sanitary napkin and ALWAYS® Regular Maxi with Wings sanitary napkin. Suitable products for use in System 3 for heavy protection needs include ALWAYS® Ultra thin Long Maxi with Wings sanitary napkin and ALWAYS® Long Super Maxi with Wings sanitary napkin, which are both manufactured and packaged under one or more of U.S. Pat. Nos. 4,342,314, 4,463,045, 4,556,146, B1 4,589,876, 4,687,478, 4,950,264, 5,009,653, 5,267,992, 5,413,568, 5,460,623, 5,462,166, 5,489,283, 5,569,231, and U.S. Pat. No. Re. 32,649.

Suitable products for inclusion in System 4 for regular protection needs include ALWAYS® Ultra thin Long Maxi with Wings sanitary napkin and ALWAYS® Long Maxi with Wings sanitary napkin. Suitable products for use in System 4 for heavy protection needs include ALWAYS® Ultra thin Overnight Maxi with Wings sanitary napkin and ALWAYS® Overnight Maxi with Wings sanitary napkin.

In a variation of the preferred embodiment described above, the available systems of feminine hygiene products may include an interlabial product or a tampon in addition to a sanitary napkin product. Suitable interlabial products for use in the systems of feminine hygiene products of the present invention are described in U.S. Pat. Nos. 3,983,873 and 4,175,561 and in U.S. patent application Ser. No. 08/778,520, filed on Jan. 3, 1997 in the name of Osborn, III.

When a tampon or interlabial product is included in a system of feminine hygiene products, the step of collecting information from a consumer regarding her body type and menstrual flow characteristics may continue to be performed in the manner described above. The step of selecting a system of feminine hygiene products is also performed as previously described, except that the appropriate system number should be decreased by one. For example, a large woman with heavy protection needs might have scored 15 total points on the table in Table 2 based upon her body size and menstrual flow characteristics. An alternative to System 4 comprising only sanitary napkins described above would be a system comprising one of the regular needs sanitary napkins described above for use in System 3 used in combination with a tampon or interlabial product. Similarly, a consumer who otherwise would be placed in System 3, could use one of the regular needs sanitary napkins described above for System 2 in combination with either a tampon or interlabial product.

In other variations of systems of feminine hygiene products comprising sanitary napkins and either tampons or interlabial products, the system number which would otherwise be selected by the table shown in Table 2 could be decreased by 2 instead of by 1 as discussed in the preceding paragraph. When using a higher absorbency tampon or a higher capacity interlabial product, a woman who might have scored 15 total points on Table 2 based upon her body size and menstrual flow characteristics could use a sanitary napkin described above as suitable for use in system 2 for regular protection needs. Such a sanitary napkin would be used in combination with either a higher absorbency tampon or higher capacity interlabial product.

It should be noted that consumers who use a system comprising a sanitary napkin used in combination with a tampon or interlabial product will not necessarily prefer to use such a combination at all times during their cycle (for example, overnight). Therefore, systems selected for such consumers could include sanitary napkins for use alone as well as a sanitary napkin for use in combination with a tampon or interlabial product. For example a consumer who might have scored 15 points on Table 2 might be provided with a system comprising the sanitary napkins described above as suitable for use in System 4. Alternatively, she could be provided with a sanitary napkin described as suitable for use in System 4 for heavy protection needs for wearing overnight. For use during the day, such a system might include a tampon or interlabial product used in combination with a sanitary napkin described as suitable for use in either System 2 or 3 for regular need times.

In additional variations of the preferred embodiment described above, Systems 1 and 2 may be combined into a single system of protection. Because only a small fraction of consumers in certain parts of the world (including North America) are expected to fall into Category 1 for most of the topics shown in Table 1, only a few consumers will have System 1 selected when performing the method of the present invention as shown in Tables 1 and 2. Therefore, it is acceptable to combine Systems 1 and 2 and use the products described above as acceptable for use in System 2 for all consumers who would otherwise be selected for System 1 or System 2.

In particularly preferred embodiments of the method of the present invention, the steps of collecting information from a consumer regarding her body size and menstrual cycle characteristics and selecting a system of feminine hygiene products are performed in a substantially continuous, interactive process. For example, the information may be collected from a consumer and a system selected through the use of an interactive store display. Such a display could be equipped with an interactive computer which will prompt the user to answer questions, keep track of the answers, and select an appropriate system based on those answers as described above. In alternative embodiments, the information may be collected from a consumer though the use of an interactive site on the World Wide Web, or through the use of an interactive menu-driven phone system. Charts, tables or other figures may be used to collect information from a consumer and take the consumer through the system selection process as described above. These charts or figures may be located on an in-store display or in in-store advertising. Similarly, charts or figures could be published in publications such as newspapers or magazines or could be mailed to potential consumers. It is also possible for information regarding the use of systems of feminine hygiene products in accordance with the method of the present invention to be distributed to providers of women's health care services. In such scenarios, the interaction described in the present application could take place between a consumer and her OB/GYN or other health care provider.

After having collected information from a consumer regarding her body size and menstrual cycle characteristics, and having selected a system of feminine hygiene products, the method of the present invention calls for providing information back to the consumer identifying the products which make up the selected system, thereby allowing the consumer to use the selected system. This provision of information may be provided through the use of packaging indicia. For example, in preferred embodiments where there are four available systems of feminine hygiene products, each of the four systems might have a unique number, color, symbol, or some combination of these, associated with it. Products which make up each of the four systems could then be packaged in packages marked with the corresponding unique number, color, or symbol.

In one preferred embodiment of the method of the present invention, the feminine hygiene products making up each of the available systems are packaged together in a common package. This allows a consumer to purchase an entire system in one package without having to assembly the required products herself. In other preferred embodiments of the method of the present invention, the feminine hygiene products making up the various available systems could be packaged individually or in packages of about 2 to 9 products per package. Such individually packaged products could be housed in a display stand which allows consumers to select a variety of products to assemble a system once information identifying those products which make up the selected system is received by the consumer. In other embodiments, the information provided to the consumer might simply be a list of the commercial names of available feminine hygiene products which make up the selected system.

TEST METHODS

Sanitary Napkin Length Measurement

The Length Measurement is performed on samples that have been conditioned by leaving them in a room at 50% relative humidity and at 73° F. for a period of two hours prior to the test. The measurement should be performed under similar conditions.

Length is measurement by fully unfolding the sample to measured so that it lays flat. The length of the product is measured from the topsheet side. When measuring, the ruler should be placed along the longitudinal centerline of the pad so as to measure the longest dimension, from the fullest part of the curvature at the ends of the sample. Align the ruler by placing the 0-point at the leading outer edge of the crimp at one end of the sample. While allowing the ruler to follow the contour of the pad surface, measure the length to the nearest ½ mm to the outer edge of the crimp at the opposite end of the sample from the 0-point of the ruler. Follow the contour of the core gently and do not press into the core.

Sanitary Napkin Area Measurement Test

Overview

This method is used to determine the two-dimensional area of samples including finished catamenial pads and pantiliners. The sample to be measured is laid flat (or taped) on a high contrast surface. For example, a white sample should be placed on a black background. A video camera with input to an image analysis computer is positioned over the product. A flatbed scanner can also be used to capture the image. The software is calibrated for distance using a standard ruler. An appropriate gray scale threshold is selected by the analyst to optimally detect the outline of the product. The area is calculated by the computer and is determined by pixel count of a digitized image.

| Apparatus | |
| --- | --- |
| Ruler | Starret C334 150 mm or equivalent |
| Scanner | HP Scanjet 3P or equivalent |
| OR | |
| Video Camera and video capture board | Hi-8 or Y/C format camera with zoom lens Data Translation DT2255–60 Hz, or equivalent |
| Image analysis computer and software | Macintosh IIci or better Image 1.44 or later version |
| Conditioned Room | Temperature and humidity should be controlled to remain within the following limits: Temperature: 73 ± 3° F. (23° C. ± 2° C.) Humidity: 50 ± 2% Relative Humidity |

Procedure

1. Lay the sample flat on a high contrast surface. The sample must be unfolded completely (i.e., wings must be unfolded and lay flat on the surface). If portions of the sample do not lay flat (for example, if the sample has been previously folded or if the sample is a curved pad) then the sample must be taped to the high contrast surface so that it lays flat.
2. Put the sample on the high contrast surface under the camera or on the scanner. Use magnification that provides adequate resolution of the object to be measured. The sample should cover at least 10% of the screen viewing area to ensure adequate resolution. A scanner at 200 dots per inch provides adequate resolution for pad samples. If a video camera is being used as an input device, the focal plane of the camera must be parallel to the sample (camera must not be at an angle to the sample).
3. Capture an image of a high quality ruler or scale that is at least half as long as the object to be measured. The calibration scale must be placed in the same plane as the objects to be measured. Calibrate the image analysis program for scale. After setting the scale in the image analysis software, scan an object of known area to verify accurate calibration.

4. Put the sample under the camera or on the scanner in place of the calibration scale. Be sure the sample is essentially planar. Tri-folded pads will have to be flattened using a weight or taped to a flat surface. Similarly wings or flaps will have to be unfolded and flattened or taped. Maximize the contrast between the sample and the background. A white sample should be placed on a black background, and the lighting should be adjusted to show a large difference in intensity without saturating either the white pad or the dark background. Careful choice of lighting will minimize interferences from shadows and glare. Capture a high-resolution image of the sample.

5. Measure the object by visually setting the gray level threshold to best match the true area of the sample. If there is not sufficient contrast, magnify the image as much as possible and trace the outermost perimeter of the sample's image on the computer monitor with the mouse. Use the image analysis software to count pixels and convert the count into area in units of square centimeters or square millimeters.

6. Report the result to the nearest 0.1 $cm^2$.

End of Test

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. A method of providing a system of using feminine hygiene products to a consumer, said method comprising the steps of:

collecting information from said consumer regarding her body size and menstrual cycle characteristics;

selecting a system of feminine hygiene products from at least two available systems, wherein each of said available systems is comprised of at least two different feminine hygiene products, and wherein each of said available systems is adapted to correspond to a predetermined range of body sizes and menstrual cycle characteristics; and providing information to said consumer regarding the products which make up said selected system thereby allowing said consumer to use said system of feminine hygiene products.

2. The method of claim 1 wherein the number of said available systems is between 3 and 6, inclusive.

3. The method of claim 2 wherein the number of said available systems is three.

4. The method of claim 3 wherein the first of said three available systems comprises a first sanitary napkin having a length between about 219 and about 249 mm and an area of between about 126 and about 224 $cm^2$, and a second sanitary napkin having a length between about 226 and about 261 mm and an area of between about 146 and about 320 $cm^2$.

5. The method of claim 3 wherein the second of said three available systems comprises a first sanitary napkin having a length of between about 232 and about 261 mm and an area of between about 146 and about 320 $cm^2$ and a second sanitary napkin having a length between about 248 and about 304 mm and an area of between about 177 and about 348 $cm^2$.

6. The method of claim 3 wherein the third of said three available systems comprises a first sanitary napkin having a length of between about 248 and about 304 mm and an area of between about 170 and about 348 $cm^2$ and a second sanitary napkin having a length greater than or equal to about 296 mm and an area greater than or equal to about 224 $cm^2$.

7. The method of claim 2 wherein the number of said available systems is four.

8. The method of claim 7 wherein the first of said four available systems comprises a first sanitary napkin having a length of between about 110 and about 244 mm and an area of between about 55 and about 242 $cm^2$ and a second sanitary napkin having a length between about 219 and about 249 mm and an area of between about 126 and about 265 $cm^2$.

9. The method of claim 8 wherein said first sanitary napkin has a length of between about 219 and about 230 mm and an area of between about 162 and about 242 $cm^2$ and said second sanitary napkin has an area of between about 162 and about 265 $cm^2$.

10. The method of claim 7 wherein the second of said four available systems comprises a first sanitary napkin having a length of between about 219 and about 249 mm and an area of between about 126 and about 224 $cm^2$ and a second sanitary napkin having a length between about 226 and about 261 mm and an area of between about 146 and about 320 $cm^2$.

11. The method of claim 10 wherein said first sanitary napkin has an area of between about 162 and about 224 $cm^2$ and said second sanitary napkin has a length of between about 238 and about 261 mm and an area of between about 220 and about 320 $cm^2$.

12. The method of claim 7 wherein the second of said four available systems comprises a first feminine hygiene product and a second feminine hygiene product, wherein said first feminine hygiene product is sanitary napkin having a length of between about 110 and about 244 mm and an area of between about 55 and about 242 $cm^2$, and wherein said second feminine hygiene product is selected from the group consisting of a tampon and an interlabial product.

13. The method of claim 7 wherein the third of said four available systems comprises a first sanitary napkin having a length of between about 232 and about 261 mm and an area of between about 146 and about 320 $cm^2$ and a second sanitary napkin having a length between about 248 and about 304 mm and an area of between about 177 and about 348 $cm^2$.

14. The method of claim 13 wherein said first sanitary napkin has a length of between about 238 and about 261 mm and an area of between about 255 and about 320 $cm^2$ and said sanitary napkin has a length of between about 255 and about 304 mm and an area of between about 302 and about 348 $cm^2$.

15. The method of claim 7 wherein the third of said four available systems comprises: a first feminine hygiene product and a second feminine hygiene product, wherein said first feminine hygiene product is sanitary napkin having a length of between about 219 and about 249 mm and an area of between about 126 and about 224 $cm^2$, and wherein said second feminine hygiene product is selected from the group consisting of a tampon and an interlabial product.

16. The method of claim 7 wherein the third of said four available systems comprises at least one sanitary napkin having a panty elastic wrapping component.

17. The method of claim 7 wherein the fourth of said four available systems comprises a first sanitary napkin having a length of between about 248 and about 304 mm and an area of between about 170 and about 348 cm$^2$ and a second sanitary napkin having a length greater than or equal to about 296 mm and an area greater than or equal to about 224 cm$^2$.

18. The method of claim 17 wherein said first sanitary napkin has a length of between about 255 and about 304 mm and an area of between about 302 and about 348 cm$^2$ and said sanitary napkin has a length of between about 300 and about 380 mm and an area of between about 314 and about 500 cm$^2$.

19. The method of claim 7 wherein the fourth of said four available systems comprises: a first feminine hygiene product and a second feminine hygiene product,
wherein said first feminine hygiene product is sanitary napkin having a length of between about 232 and about 261 mm and an area of between about 146 and about 320 cm$^2$, and
wherein said second feminine hygiene product is selected from the group consisting of a tampon and an interlabial product.

20. The method of claim 7 wherein the fourth of said four available systems comprises at least one sanitary napkin having a panty elastic wrapping component.

21. The method of claim 1 wherein the steps of collecting information from a consumer and selecting a system of feminine hygiene products are performed using a computer.

22. The method of claim 1 wherein the steps of collecting information from a consumer and selecting a system of feminine hygiene products are performed using an interactive in-store display.

23. The method of claim 1 wherein the steps of collecting information from a consumer and selecting a system of feminine hygiene products are performed using a telephone system.

24. The method of claim 1 wherein the step of providing said information to the consumer regarding the products which make up said system of feminine hygiene products is accomplished through the use of packaging indicia.

25. The method of claim 1 wherein said feminine hygiene products comprising each of said individual systems are packaged in a common package.

26. A method of using a system of feminine hygiene products by a consumer, said method comprising the steps of:
providing information regarding the consumer's body size and menstrual cycle characteristics to a system selection interface;
said system selection interface selecting a system of feminine hygiene products from at least two available systems, wherein each of said available systems is comprised of at least two different feminine hygiene products, and wherein each of said available systems is adapted to correspond to a predetermined range of body types and menstrual cycle characteristics; and
receiving information from said system selection interface regarding the products which make up said selected system thereby allowing the consumer to use said system of feminine hygiene products.

27. The method of claim 26 wherein said system selection interface comprises an interactive computer.

28. The method of claim 26 wherein said system selection interface comprises a modified slide-rule type device.

29. The method of claim 26 wherein said system selection interface comprises a printed chart and accompanying instructions for use.

30. A method of providing a system of using feminine hygiene products to a consumer, said method comprising the steps of:
collecting information from said consumer regarding her body size;
selecting a system of feminine hygiene products from at least two available systems, wherein each of said available systems is comprised of at least two different feminine hygiene products, and wherein each of said available systems is adapted to correspond to consumers falling within a predetermined range of body sizes; and
providing information to said consumer regarding the products which make up said selected system thereby allowing said consumer to use said system of feminine hygiene products.

31. A method of providing a system of using feminine hygiene products to a consumer, said method comprising the steps of:
collecting information from said consumer regarding her menstrual cycle characteristics, said information including more than the perceived flow of the consumer without more, and wherein at least some of said information collected includes objective data expected to be readily known by most consumers using the method;
selecting a system of feminine hygiene products from at least two available systems, wherein each of said available systems is comprised of at least two different feminine hygiene products, and wherein each of said available systems is adapted to correspond to consumers falling within a predetermined range of menstrual cycle characteristics; and
providing information to said consumer regarding the products which make up said selected system thereby allowing said consumer to use said system of feminine hygiene products.

* * * * *